United States Patent [19]

Schnitzler

[11] Patent Number: 4,534,075
[45] Date of Patent: Aug. 13, 1985

[54] STRETCHER HAVING BACKREST AND SAFETY HARNESS

[75] Inventor: Alois Schnitzler, Bonn, Fed. Rep. of Germany

[73] Assignee: Christian Miesen Fahrzeug-Und Karosseriewerk GmbH, Bonn, Fed. Rep. of Germany

[21] Appl. No.: 361,906
[22] PCT Filed: Jun. 30, 1981
[86] PCT No.: PCT/DE81/00103
  § 371 Date: Mar. 11, 1982
  § 102(e) Date: Mar. 11, 1982
[87] PCT Pub. No.: WO82/00247
  PCT Pub. Date: Feb. 4, 1982

[30] Foreign Application Priority Data

Jul. 11, 1980 [DE] Fed. Rep. of Germany ....... 3026406
Nov. 6, 1980 [DE] Fed. Rep. of Germany ....... 3041932
Jun. 22, 1981 [DE] Fed. Rep. of Germany ....... 3124416

[51] Int. Cl.³ .............................................. A61G 1/00
[52] U.S. Cl. .......................................... 5/82 R; 5/89; 5/72; 5/434; 296/20
[58] Field of Search ....................... 5/70–72, 5/82 R, 82 B, 431, 434, 437; 297/393, 397, 399, 409, 485, 484; 296/20

[56] References Cited

U.S. PATENT DOCUMENTS

| 1,874,613 | 8/1932 | Pilates | 297/404 |
| 2,033,779 | 3/1936 | Monk | 5/82 |
| 2,191,097 | 2/1940 | Morrison | 5/434 |
| 2,309,464 | 1/1943 | Lucci | 5/82 |
| 2,361,328 | 10/1944 | Springer | 5/82 |
| 2,666,476 | 1/1954 | Lycan | 297/404 |
| 2,973,029 | 2/1961 | Schlosstein | 297/404 |
| 3,204,256 | 9/1965 | Stollenwerk | . |
| 3,347,544 | 10/1967 | Uffenorde | 5/434 |
| 3,561,817 | 2/1971 | Needham | 297/484 |
| 3,566,422 | 3/1971 | Klippel | 5/82 |
| 3,707,734 | 1/1973 | Matthews | 5/82 |
| 3,732,863 | 5/1973 | Harrington | . |
| 3,737,923 | 6/1973 | Prolo | 5/82 |
| 3,779,599 | 12/1973 | Gotlfried | 297/397 |
| 3,819,197 | 6/1974 | Shakespear | 297/484 |
| 3,887,233 | 6/1975 | Garavaglia et al. | 297/484 |
| 3,918,760 | 11/1975 | Goldberg | 297/484 |
| 4,034,748 | 7/1977 | Winner | 5/434 |
| 4,064,574 | 12/1977 | Schnitzler | 5/82 R |
| 4,074,373 | 2/1978 | Garofalo | 5/434 |
| 4,124,908 | 11/1978 | Burns et al. | . |
| 4,151,842 | 5/1979 | Miller | 5/82 B |
| 4,175,787 | 11/1979 | Muskat | 297/484 |
| 4,204,529 | 5/1980 | Cochrane | . |
| 4,285,545 | 8/1981 | Protze | 297/483 |

FOREIGN PATENT DOCUMENTS 611065 12/1960 Canada .............................. 297/484

Primary Examiner—Gary L. Smith
Assistant Examiner—Michael F. Trettel
Attorney, Agent, or Firm—Armstrong, Nikaido, Marmelstein & Kubovcik

[57] ABSTRACT

The invention is with respect to a stretcher for ambulances. The stretcher has a backup or retainer cushion for keeping a patient in position when acted upon by jerks or by sudden motion in the length-direction of the ambulance. The backup cushion is united with a safety belt, which is so placed on the patient that the patient is kept in position in relation to the stretcher when suddenly jerked in the length-direction. In the case of one form of the invention, the backup cushion is elastically supported so that the body of the patient is not suddenly slowed down. As part of a useful further development of the invention, the backup cushion is joined with a fixing belt, which, for its part, is drivingly joined up with the lock or ratchet of an automatic belt take-up roller or pulley. This roller itself has a safety belt which, on loading the stretcher onto a stretcher support of the ambulance, is joined up with the floor of the vehicle, more specially automatically. The design is such that, when the fixing belt is acted upon by a sudden pulling force on decelerating at more than a certain rate, the automatic belt roller is locked by way of the lock. Because of this, the patient and the stretcher are safely kept in position. The design may furthermore be used in connection with stretchers designed as day-beds.

34 Claims, 9 Drawing Figures

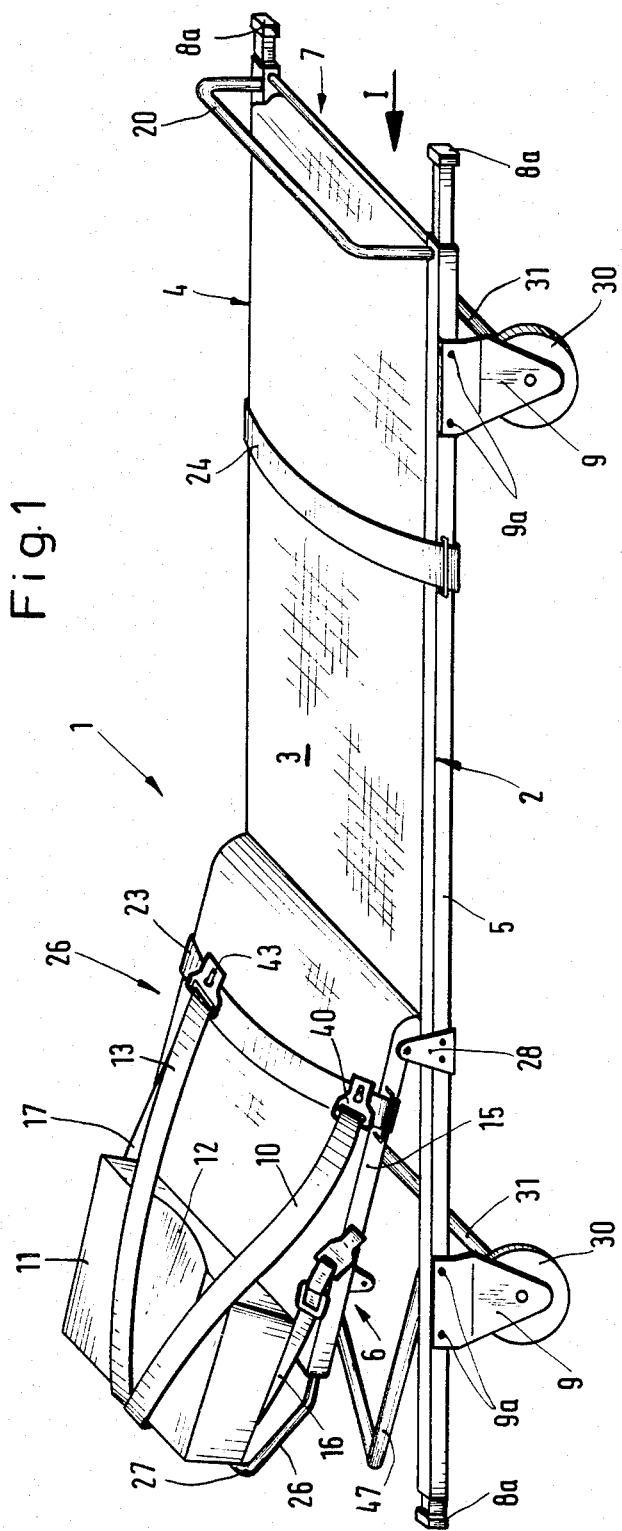

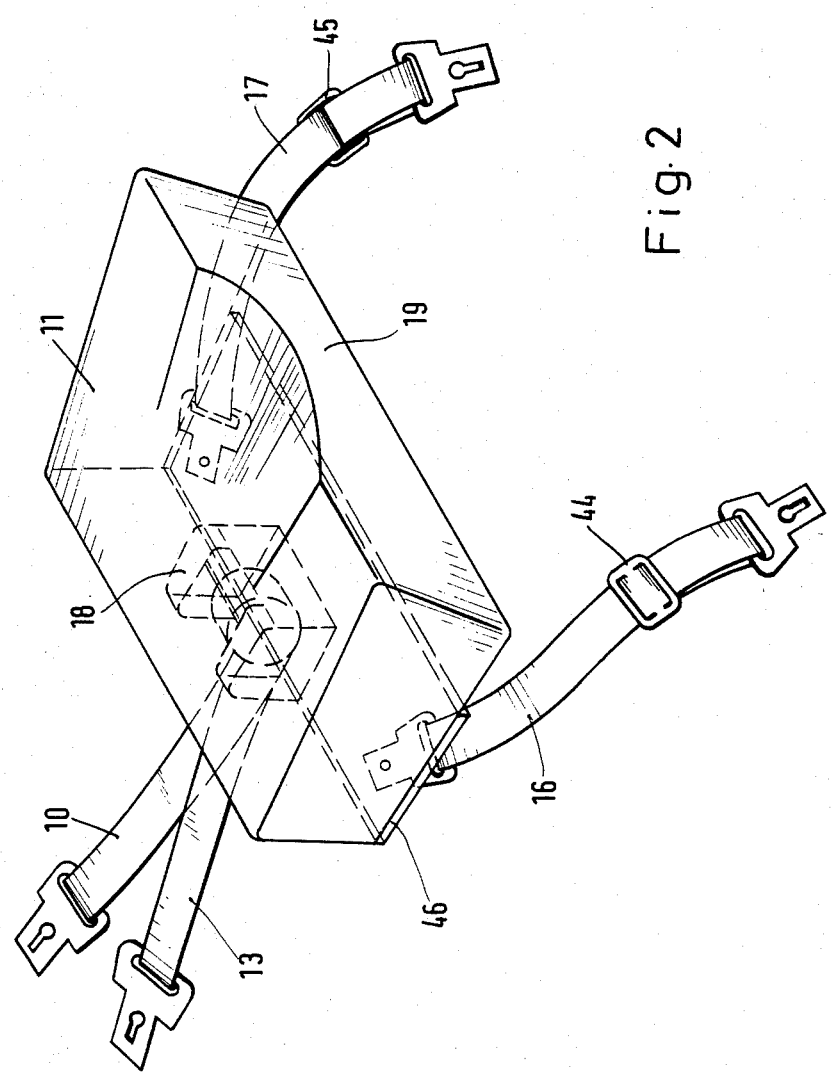

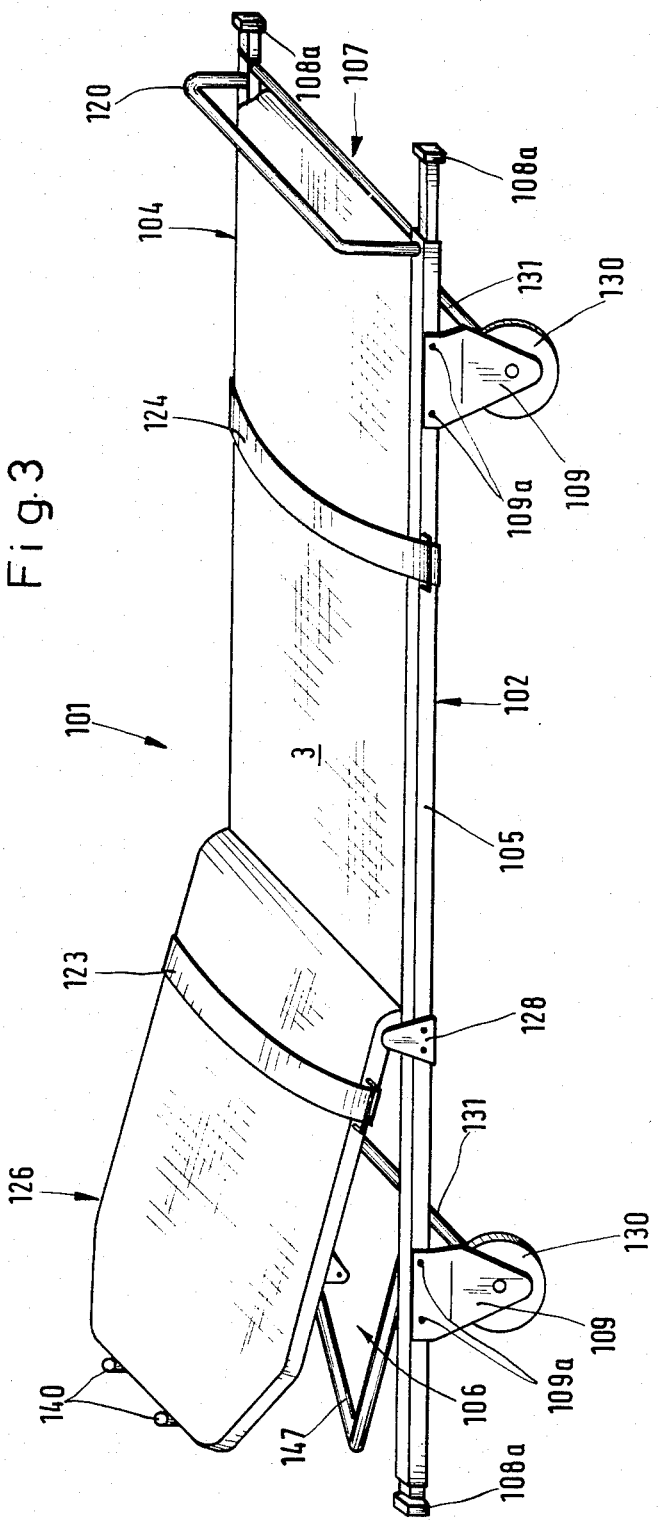

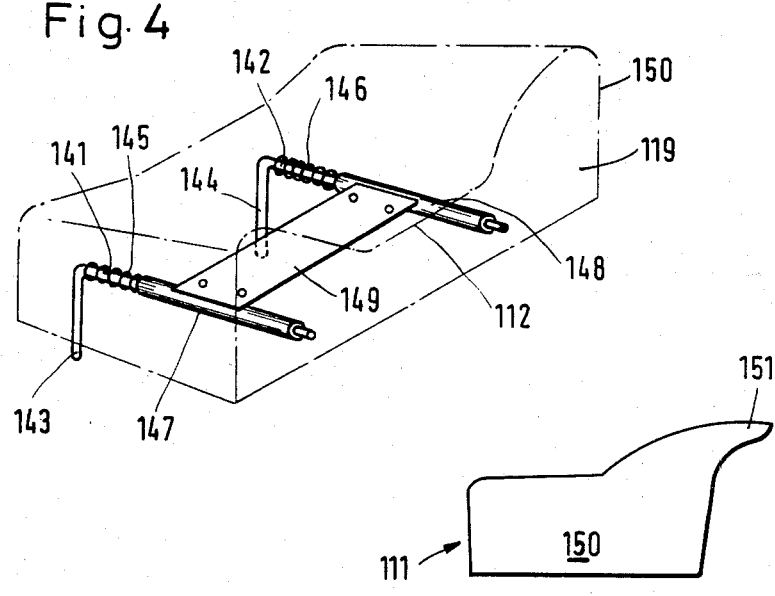
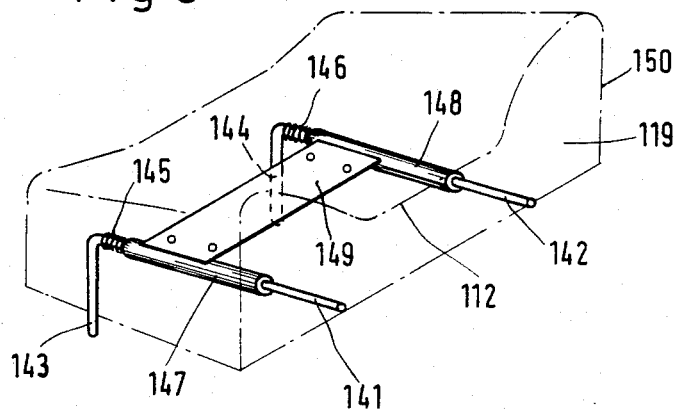

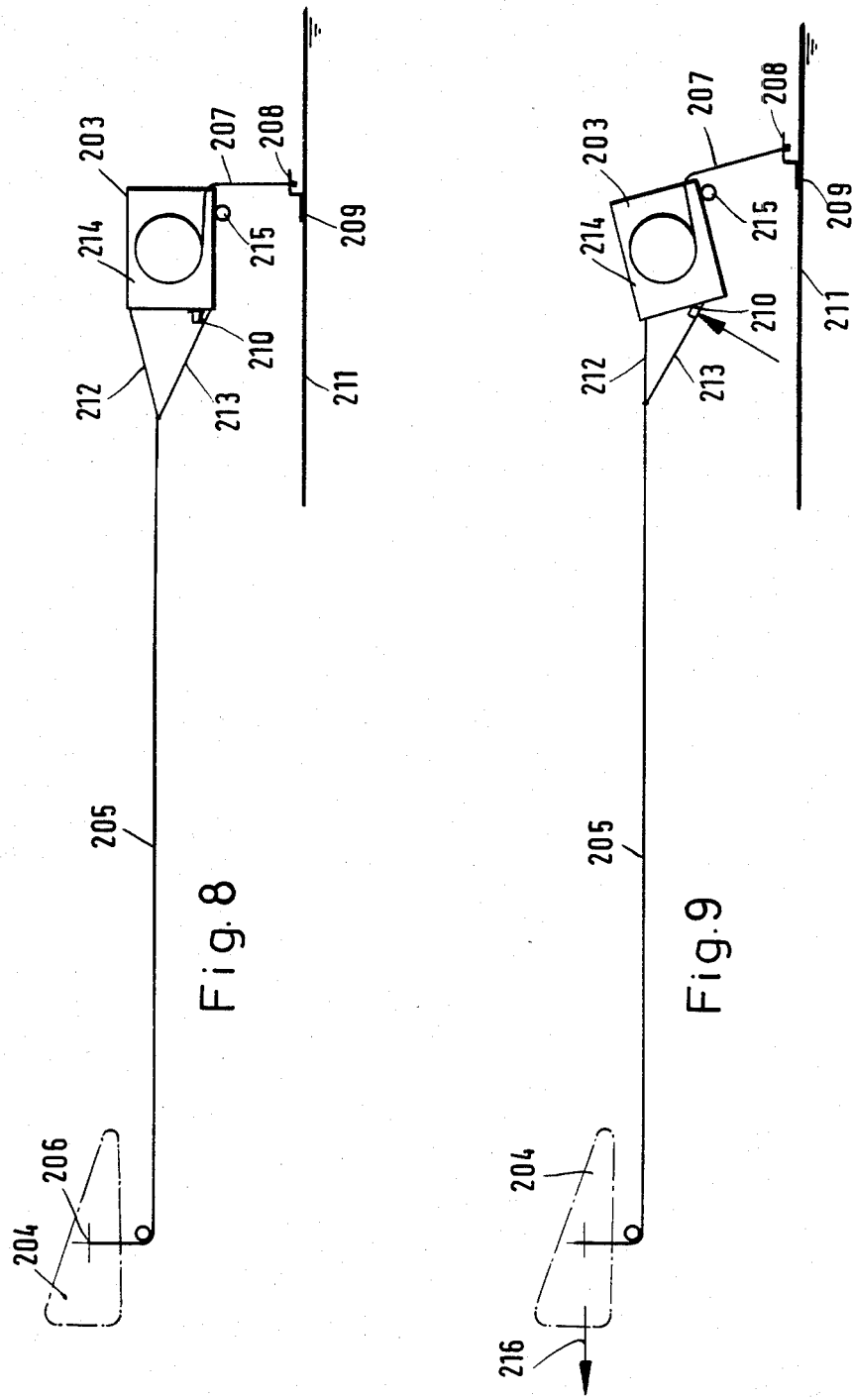

STRETCHER HAVING BACKREST AND SAFETY HARNESS

BACKGROUND OF THE INVENTION

The present invention is with respect to a stretcher with an adjustable belt designed for use as a safety belt for a patient using the stretcher.

On transporting persons on stretchers in an ambulance, there is a chance, from time to time, of the ambulance being voilently slowed down, as for example on smashing up against something in its way in a road accident. For stopping injuries to the patient in such a case, there has been a suggestion (see German Pat. No. 2,543,473) to have a belt sloping over one shoulder of the patient and fixed to the head end of the stretcher so that the patient's shoulder is kept at least 20 cm from the head end. This distance of 20 cm is in fact a lower limit for the distance between the patient's shoulder and the head end. On an ambulance (transporting a stretcher on which a patient is safety belted by using such a sloping shoulder belt) crashing up against something in its way, the patient will firstly be forced forwards through this distance of about 20 cm before being stopped by the safety belt; it may then be that his or her head will be even pushed over and past the head end of the stretcher so that it will no longer be supported.

For getting round such shortcomings, I have, in the past, designed a system in which the safety belt was to be fixed at shoulder level, this, however, limiting the width of the stretcher for supporting the patient; furthermore it seemed likely that, if the stretcher was, in effect, made narrower for the patient, there would be a greater chance of patient injury. It would furthermore have been possible for the safety belt to have been trained round under the stretcher, that is to say not at its head end, for which purpose, however, the safety belt would have to have been threaded through holes in the cover sheet on the stretcher and the support thereunder. Because, however, the support is to be able to be taken off again, it would seem to be a waste of time and unnecessarily complex for the safety belt to have to be threaded through the cover sheet and into the support every time the stretcher is used. Furthermore, the support and the cover of the stretcher would have to have special holes for this.

GENERAL OUTLINE OF THE INVENTION

For this reason, the purpose of the invention is that of designing a stretcher of the sort noted, in the case of which there is no chance of injury to the patient even when there is a sudden, sharp motion of the stretcher in the length direction. For effecting this purpose, the safety belt is united with a backup cushion on which the patient is so rested that, even on sudden forces acting in the length-direction of the stretcher, the patient is kept in position on the stretcher.

In the case of the invention it is, in fact, possible to say that the safety belt is united with a backup or stop cushion to make up inertia forces when the ambulance is violently slowed down or speeded up.

More specially, it is possible for the backup cushion to be designed so that the shoulders of the patient are supported on it on a backup face, the cushion being inwardly curved for the head and neck of the patient.

As a further useful development of the invention, the stretcher has a further safety belt, which, like the first-noted safety belt, is run over one shoulder in each case of the patient. The safety belt and the further safety belt are, in this case, each fixed at one end on the backup cushion while the other ends of the two belts are fixed to said rails of the stretcher at its head end. The other end of the two safety belts may, in this respect, be fixed on the side rails at the same level as a fixing belt, running across the stretcher. It is furthermore possible for the first safety belt and the further safety belt noted to be joined to the fixing belt itself.

A useful effect may furthermore be produced if at least one belt is used for fixing the backup cushion on the stretcher. This belt, and possibly a further belt, will, in this case, be able to be fixed on one side rail or bar of the head end of the stretcher.

The safety belt, and the further safety belt, if any, may be joined with the backup cushion by way of an automatic belt roller. As a last point, a useful effect is produced if the safety belt and the belts used for fixing the backup cushion in position may be adjusted in their length.

For stopping, on the one hand, the patient from being violently decelerated in a smash-up or because of the driver's reactions when there is a danger of a smash-up, and on the other hand for making it readily possible for the cover of the mattress on the stretcher to be readily changed, in a preferred form of the invention the backup or stop cushion is elastically supported so that patient is not violently decelerated on very sharp braking of the ambulance taking place or on the ambulance's plowing into something.

Because, as part of the invention, the backup cushion is elastically supported, it is possible for the force of the patient's body caused by inertia, to be taken up smoothly and without injury by the elastic support used for the backup cushion; furthermore, the stretcher of the present invention makes the work of the ambulanceman much simpler, inasmuch as covering over the mattress on the stretcher with a sheet or a length of paper may be done without first taking off the backup cushion. Lastly, the backup cushion may be fixed on prior art stretcher without many changes having to be made on such stretchers or vehicles for this purpose.

It may be seen that in fact in the invention the backup cushion is not united with the safety belt as a single structure and, in fact, the cushion is elastically or springingly supported, for example by a spring. The spring may, for its part, be placed on a plunger system which, to good effect, may be united with the backup cushion.

It is best for the plunger system to be able to be fixed at the head end of the stretcher, it having two plungers running in the length-direction of the stretcher, one plunger casing with the spring sliding on each plunger. It is possible for the two plunger housings to be joined rigidly by a plate with each other.

The plunger system or the spring system will be placed under the cushion in the limited sense of the word. In this respect, the plunger system may be placed on the lower side of a wood board having reinforcing bars and having on its top side a cast hard foam molding which, in its part answering to the patient's head, is covered with soft foam. The hard foam molding, together with the soft foam, is covered over with leather-cloth which is fixed to the lower edge of the board.

The backup cushion has a cushioning wall for stopping any slipping of the body of a patient over the backup cushion, this being because, in view of the fact that the backup cushion may be moved along the length of the plungers, no safety belts may be used.

The design may be made even safer with respect to stopping injuries to a patient transported on such a stretcher by having the backup cushion fixed to a keeper belt, a safety belt with an automatic roller for belt take-up and a coupling part, a second coupling part on the floor of the vehicle, with which the coupling part of the safety belt becomes coupled on putting the stretcher onto a stretcher support, the keeper belt being so joined with the automatic roller for taking up the belt that the automatic roller will be locked when pulled upon by the keeper belt.

This design gives the useful effect, more specially that on deceleration at greater than a given value, or if the stretcher comes off the system supporting it, the patient will still go on being kept in position by the stretcher even on the floor of the vehicle. A further useful effect is that the safety belt is joined up, for the time being, by way of a coupling with the floor of the vehicle when the stretcher is being put into the vehicle. The keeper belt, joined with the automatic roller and with the backup cushion, will have the effect of locking the automatic belt take-up roller when the backup cushion is violently moved so that the safety belt, joined with the floor of the vehicle, will be locked and the patient, together with the stretcher, will be kept in position on the ambulance floor without slipping. A special, useful effect of the system in this form is that, in the case of systems, in which the stretchers are pulled forward or are put on the ambulance with the head of the patient lower down than the rest of his body, the automatic take-up roller makes possible such normal motion and it is only on violent changes in speed, for example when braking sharply or in a smash-up, that the automatic roller is automatically locked.

With respect to details of this design of the invention, it is possible for the automatic belt take-up roller to be placed on a cross-bar of the stretcher near the foot end. This makes certain that, on putting the stretcher on the ambulance, it is quite simple to take a look to see that the safety belt is in fact joined with the floor of the vehicle.

In a more specially preferred example of the invention the keeper belt is trained round under the stretcher.

It is furthermore useful, as a detail of design, for the keeper belt to be designed branching out sideways at the head end of the stretcher and to have connections on the two sides of the backup cushion. This makes certain that the backup cushion is very strongly kept in position.

The connections are best made so that they may be undone for the purpose of putting on and taking off covers (such as a mattress cover) simply.

As part of a more specially preferred working example of the invention, the coupling part of the safety belt may take the form of a keeper loop while the coupling part on the floor of the vehicle is in the form of a hook or the like, into which the keeper loop may be automatically fixed.

In this respect, a specially useful effect is produced if the rolled-up length of the safety belt is so limited that in the rolled-up condition, the keeper loop is at a small distance along the floor of the vehicle. With this special form of the invention, very simple self-locking of the safety belt in position is made certain of.

One working example of the invention may be so designed that the keeper belt is joined up with the lock of the automatic take-up roller itself.

An other possible way of doing this, giving a useful effect, is one in which the keeper belt is forked at the foot end of the stretcher upwards and downwards, one branch of the fork being joined with the lock and the other being designed for taking up the pulling forces. A form of the invention which is more specially to be preferred to this is one in which the keeper belt is forked with branches stretching upwards and downwards, at the foot end of the stretcher, in such a way that the two branches of the fork are fixedly joined with the housing of the automatic take-up roller, one of the braches being so placed that a change in angle between the branches puts the lock of the automatic belt take-up roller into operation.

The useful effects of the present invention may furthermore be produced on using the designs of the invention in the case of stretchers furthermore as seats.

LIST OF FIGURES

Further useful details of the invention will be seen from the claims.

A detailed account will now be given of some working examples of the invention using the figures.

FIG. 1 is a perspective view of a stretcher of the present invention.

FIG. 2 is a view of the backup cushion of the stretcher of FIG. 1 to make clear further details.

FIG. 3 is a view of a stretcher on which the backup cushion may be fixed.

FIGS. 4 and 5 are views of the backup cushion with its springs in the stretched-out and forced-together conditions.

FIG. 6 is a side view of the backup cushion with a cushioning wall.

FIG. 8 is a diagrammatic view to make clear the teaching of FIG. 7, in the resting condition.

FIG. 9 is a view on the same lines as in FIG. 8 when the ambulance is braked or on crashing into something.

DETAILED ACCOUNT OF WORKING EXAMPLES OF THE INVENTION

Figure 7:
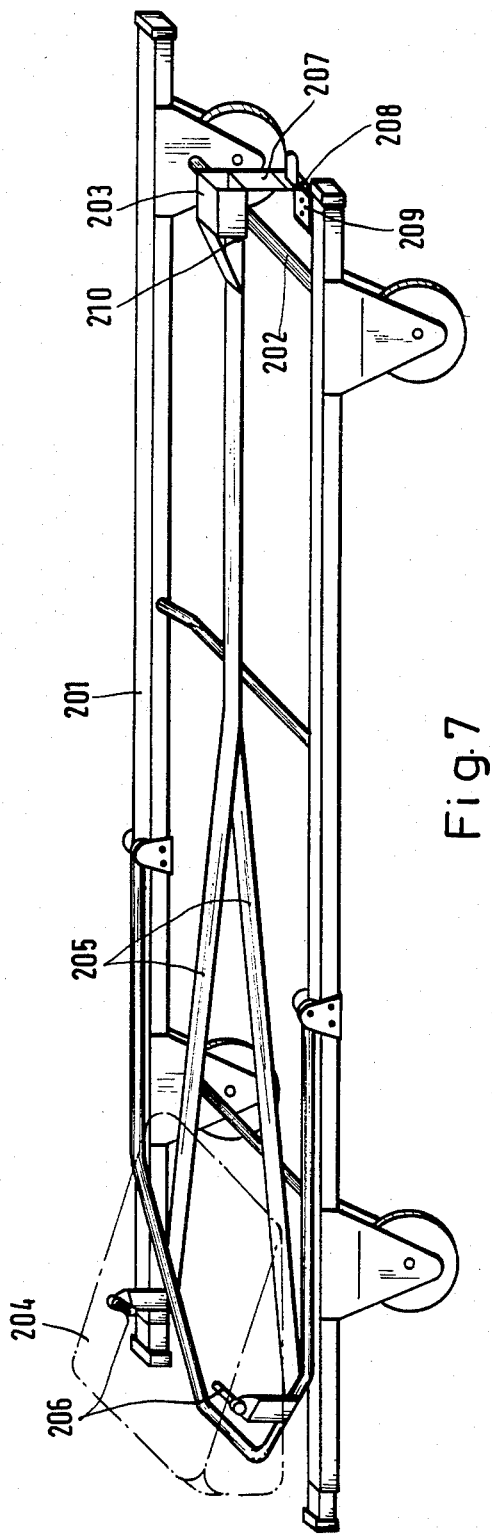
FIG. 7 is a diagrammatic perspective view of details of design of a further working example of the invention.

FIG. 1 is a view of one working example of a stretcher 1 as may be used more specially in ambulances. Stretcher 1 is made up of a support frame 2 between which there is a free, generally flat, support 3 for a patient (not figured). Generally flat support 3 will in this case be in the form of a piece of cloth which is fixed to the support frame. The support frame 2 itself is made up of side rails or bars 4 and 5 in the form of round pipes or tubes, although other cross-sections than round would be possible. At the head end 6 and at the foot end 7 of the stretcher 1, handles will be seen which may be pulled out of side rails 4 and 5 somewhat and which, at their ends, have heads 8a, limiting the degree to which the handles may be pushed into the side rails 4 and 5. The moving handles furthermore have stops (not figured) so that they may not be fully pulled out of the side rails 4 and 5. Side rails 4 and 5 furthermore have support plates 9 at the head end 6 and the foot end 7 of the stretcher 1, such support plates 9 being fixed on by screws or rivets 9a or by welding. At the lower end of support plates 9 there are wheels 30, which, in the present case, are fixed on axles 31 stretching between the two support plates 9 in each case at the head end 6 and the foot end 7 and fixed in the same.

The stretcher 1 of FIG. 1 furthermore has an upwardly folding bracket 26 made up of two side bars 14, which are joined at their ends with a crosspiece 27, and of which only one is to be seen. Part of the support 3 is placed between side bars 15. The lower ends of the side bars 15 are turningly joined to the side rails 4 and 5 by way of connections 28. Between the side rails 4 and 5 there will be seen a U-like crosspiece 20 forming a foot support for a patient resting on the stretcher 1, and a fixing or patient belt 24 used for keeping the patient's legs in position. Furthermore, between the side bars 15 there is a patient belt 23 for strapping round the top part of the patient's body.

In the case of this working example of the invention, two safety belts 10 and 13, running from fixing connections (more specially in the form of quick-release connections) 40, 43 are trained over separate shoulders of the patient and then downwards towards the lower side of a backup cushion 11. On the backup cushion 11 the safety belts 10 and 13 are fixed by an automatic belt take-up roller 18 (see FIG. 2). Backup or retainer cushion 11 has a hollow 12 for the head and neck of the patient, the shoulders of such a patient on stretcher 1 will be resting on the backup or retaining face 19 (see FIG. 2) of backup cushion 11, the safety belts 10 and 13 being trained, in each case, over one shoulder of the patient. The fixing belt 23 is furthermore trained round the patient's chest. The connections 40, 43 may, in this case, be joined to the fixing belt 23. Furthermore, belts 16, 17 will be seen which, like belts 10 and 13, may be changed in length using buckles 44, 45. Belts 16 and 17 are fixed to a base 46 of backup cushion 11, the automatic belt take-up roller 18 being fixed to base 46 as well. This base 46 is, unlike the backup cushion 11, stiff in structure. Furthermore, belts 16 and 17 may be fixed to the side bars 15 of the backrest 26, which may be changed in height using a mechanical system 47.

If the stretcher 1 is violently slowed down in the direction of arrow I, the backup face 19 of the backup cushion 11 will take up the force produced by the patient's body caused by inertia, by way of safety belts 10 and 13, so that the patient will be kept in place on and in relation to the stretcher 1. For this reason, injury to the patient by violent motion of the stretcher 1 may be generally stopped.

The stretcher 101, to be seen in FIG. 3 is made up of a support frame 102 between which there is a free, generally flat, support for a patient (not figured). Generally flat support 103 will generally be in the form of a piece of cloth which is fixed to the support frame 102. The support frame 102 itself is made up of side rails or bars 104 and 105 in the form of round pipes of tubes, although other cross-sections than round would be possible. At the head end 106 and at the foot end 107 of the stretcher 101, handles will be seen which may be pulled out of side rails 104 and 105 somewhat and which, at their ends, have heads 108a, limiting the degree of which the handles may be pushed into the side rails 104 and 105. The moving handles furthermore have stops (not figured) so that the said handles may not be fully pulled out of the side rails 104 and 105. Side rails 104 and 105 furthermore have support plates 109 at the head end 106 and the foot end 107 of the stretcher 101, such support plates 109 being fixed on by screws or rivets 109a or by welding. At the lower end of support plates 109 there are wheels 130, which, in the present case, are fixed on axles 131 stretching between the two support plates 109 in each case at the head end 106 and the foot end 107, fixed in the same.

The stretcher of FIG. 3 furthermore has an upwardly folding bracket 126 which, at its top end has eyes 140 into which ends of tubes 143, 144, may be slipped. Backrest 126 is turningly supported in connections 128 which, for their part, are fixed on side rails 104 and 105. Between the side rails 104 and 105 there is placed furthermore a crosspiece 120 forming a foot support for a patient using the stretcher 101. Furthermore, stretching between side rails 104 and 105, there is a fixing belt 124 used for keeping the legs of the patient in position. A further fixing belt 123 will be seen fixed to the backrest 126 for supporting and positioning the chest of the patient. The backrest 126 itself may be changed in height using a mechanical system 147.

FIG. 4 is a view of the backup cushion for the stretcher of FIG. 3, the cushion having two plunger rods 141 and 142 whose downwardly bent ends 143, 144 may be pushed into the openings of eyes 140. On each plunger rod 141, 142, there is a spring 145 and, in the other case, there furthermore being plunger casings 147, 148 sliding on plunger rods 141 and 142 to the back of springs 145, 146. The plunger casings 147, 148 are joined together by a plate 149. The diameter of the plunger housings or casings 147 and 148 is such that the spring 145 or 146 may be forced together within the plunger casings, as will be seen from FIG. 5. Plunger rods 141, 142, springs 145 and 146 and plunger casings 147 and 148 may be seen from this to take the form of shock absorbers in the sense that violent forces are taken up by the springs, the springs being seen in the force-free condition in FIG. 4 and in the forced-together condition in FIG. 5.

Backup cushion 111 has a hollow 112, lined with soft foam, in a hard foam molding 150 which is marked in broken lines in FIGS. 4 and 5, hollow 112 being designed for taking up the head and neck of the patient, whose shoulders, as he is supported on the stretcher 101, would be supported on a "hard" backup face 119 of backup cushion 111, belt 123 being trained round the chest or top of the body of the patient.

The molding 150 is fixed on a board (not figured), whose lower side, possibly reinforced, is joined up with parts 141 and 142. Furthermore, molding 150 is covered with leathercloth fixed to the lower side of the board. The board may be made of wood or synthetic resin.

FIG. 6 is a further side view of the backup or retainer cushion with a cushioning wall 151 filled with cushion stuffing, wall 151 being for stopping the body of a patient slipping up over the backup cushion 111, this being necessary because, in this case, no special safety belts are used for the backup cushion 111, such cushion in fact being able to be moved along the distance for which the plunger rods 141, 142 are designed for.

FIG. 7 is a diagrammatic, perspective view of a stretcher of the invention to make clear the frame only of the stretcher 201 without the board-like structures for supporting the patient. In the case of this form of the invention of FIG. 7, there is an automatic belt take-up roller 203 on a back crosspiece 202 near the foot end of stretcher 201. Roller 203 is for taking up a safety belts 207 and may be turned about a shaft 215. Automatic take-up roller 203 is joined up with the backup cushion 204 by way of a keeper belt 205, which is forked horizontally, the fork opening towards a front part, that is to say the head end of stretcher 201, the two branches of the fork of the fixing belt 205 joining at the sides by way of connections 206 with the backup or retainer cushion.

The connections 206 are best made so that they may be taken off so that the cushion 204 or the cushion cover may be readily changed As the reader will see, fixing belt 205 is placed running under the patient support (not figured) of the stretcher 201.

Safety belt 208 has a connection part 208 or keeper loop, which, in the present working examples takes the form of a connection loop for use with an other coupling part on the floor 211 of the ambulance, in the form of a hooked nose-piece 209.

As will be seen, automatic belt take-up roller 203 is so placed that, with part of the safety belt 207 rolled up and the other part pulled tight, the keeper loop 208 is spaced only a small distance from the ambulance floor 211. On pushing the stretcher 201 onto stretcher support rails (not figured) in the ambulance, the keeper loop 208 is, for this reason, automatically hooked onto nosepiece 209.

As will furthermore be seen, fixing belt 205 is vertically forked near the automatic belt take-up roller or pulley and so joined with the housing of the same that on pulling tight fixing belt 205, the lock or ratchet 210 of the take-up roller is worked.

This function is to be seen in FIGS. 8 and 9, FIG. 9 making clear what takes place when the ambulance is braked, see arrow 216.

In the working example to be seen in the figures, the branches 212 and 213 of the vertical fork of the fixing belt 205 are fixedly joined to the housing 214 of the automatic belt take-up roller 213, the design being such (see FIG. 9) that, on motion of stretcher 201 in the direction of arrow 216, the change in angle caused by this between branches 212 and 213 is responsible for working the lock 210 on the automatic belt take-up roller 203. Because on braking the ambulance at over a certain g-value, the fixing belt 205 is pulled forward by the stretcher 201 in the direction of arrow 216, the lock 210 or ratchet is turned upwards by the lower branch 213 and the safety belt locked.

In the case of further possible forms of the invention, the fixing belt 205 may be joined directly with the lock 210 or one of the branches 212 or 213 may be joined with the lock 210.

In the case of a further, somewhat changed form of the invention (not to be seen in the figures) the cushion 204 is designed so that not only one but its two sides may be used, in which respect, one side of cushion 204 has a hollow for the head while the opposite side is smoothly cushioned, that is to say without hollows.

As a further change in the forms of the invention to be seen in the figures and of which an account has been given, a useful effect is produced on using the design of a backup cushion as noted in the case of stretchers designed as seats or day-beds.

I claim:

1. A stretcher having an adjustable belt for use as a safety belt for keeping a patient in position comprising:
   a back cushion, said safety belt attached to said backup cushion for a patient's body and means mounting said backup cushion to said stretcher such that a patient resting against it is kept in a position relative to said stretcher, even when subjected to a sudden motion in the lengthwise direction, toward the head of the patient said backup cushion comprising a backup face means, engageable with the top portion of the shoulders of a patient, for restraining movement of said shoulders past said cushion, and a hollow portion to accomodate the head and neck of a patient.

2. A stretcher as claimed in claim 1, including a second safety belt, also adjustable and united with said backup cushion.

3. A stretcher as claimed in claim 2, wherein said safety belt and said second safety belt are each adapted to be trained over a different shoulder of the patient.

4. A stretcher as claimed in claim 1, including at least one attaching belt for attaching said backup cushion to said stretcher.

5. A stretcher as claimed in claim 4, wherein said attaching belt is fixed to one of said siderails.

6. A stretcher as claimed in claim 4, wherein said attaching belt is adjustable in length.

7. A stetcher having an adjustable belt for use as a safety belt for keeping a patient in position, comprising:
   a backup cushion united with said safety belt for a patient's body and disposed on said stretcher such that a patient resting against it is kept in a position relative to said stretcher, even when subjected to a sudden motion in the lengthwise direction toward the head of the patient, said backup cushion comprising a backup face means, engageable with the top portion of the shoulders of a patient, for restraining movement of said shoulders past said cushion, and a hollow portion to accommodate the head and neck of a patient;
   a second safety belt, also adjustable and united with said backup cushion, said safety belt and said second safety belt are each adapted to be trained over a different shoulder of the patient; and
   a backrest disposed on said stretcher and adapted to be inclined to raise the torso and head of the patient, siderails extending longitudinally along each side of said backrest and each of said safety belts having one end fixed to said backup cushion and having opposite ends thereof each attached to one of said siderails.

8. A stretcher as claimed in claim 7, including a fixing belt disposed laterally across said backrest and fixed to said siderails such that said opposite ends of said safety belts are fixed to said siderails at the same level as said fixing belt.

9. A stretcher as claimed in claim 8, wherein said safety belts are fixed directly to said fixing belt.

10. A stretcher having an adjustable belt for use as a safety belt for keeping a patient in position, comprising:
    a backup cushion united with said safety belt for a patient's body and disposed on said stretcher such that a patient resting against it is kept in a position relative to said stretcher, even when subjected to a sudden motion in the lengthwise direction toward the head of the patient, said backup cushion comprising a backup face means, engageable with the top portion of the shoulders of a patient, for restraining movement of said shoulders past said cushion, and a hollow portion to accommodate the head and neck of a patient; and
    wherein said safety belt and a second safety belt are joined by way of an automatic belt take-up roller to the backup cushion.

11. A stretcher having an adjustable belt for use as a safety belt for keeping a patient in position, comprising:
    a backup cushion united with said safety belt for a patient's body and disposed on said stretcher such that a patient resting against it is kept in a position relative to said stretcher, even when subjected to a sudden motion in the lengthwise direction toward the head of the patient, said backup cushion comprising a backup face means, engageable with the top portion of the shoulders of a patient, for restraining movement of said shoulders past said cushion, and a hollow portion to accommodate the head and neck of a patient; and wherein the backup cushion is elastically supported on the stretcher, so that the body of the patient is gradually accelerated or decelerated upon sudden movements of the stretcher, such as a sudden stop or start of an ambulance.

12. A stretcher as claimed in claim 11, wherein said backup cushion is elastically supported by at least one spring.

13. A stretcher as claimed in claim 12, including a plunger assembly which contains said one spring.

14. A stretcher as claimed in claim 13, wherein said plunger assembly is integral with said backup cushion.

15. A stretcher as claimed in claim 14, wherein said plunger assembly is adapted to be fixed to the end of the stretcher which receives the head of the patient.

16. A stretcher having an adjustable belt for use as a safety belt for keeping a patient in position, comprising:
a backup cushion united with said safety belt for a patient's body and disposed on said stretcher such that a patient resting against it is kept in a position relative to said stretcher, even when subjected to a sudden motion in the lengthwise direction, toward the head of the patient, said backup cushion comprising a backup face means, engageable with the shoulders of a patient, for restraining movement of said shoulders past said cushion, and a hollow portion to accommodate the head and neck of a patient, and wherein said backup cushion is elastically supported on the stretcher, so that the body of the patient is gradually accelerated or decelerated upon sudden movements of the stretcher, such as the surge of an ambulance, said cushion also including a plunger assembly fixed to the end of the stretcher which receives the patient's head, and integral with said backup cushion, said plunger assembly comprising:

a plurality of plunger rods extending longitudinally with respect to the stretcher and attached therto;
a plurality of plunger casings attached to said backup cushion and adapted to be fit around each plunger rod respectively and to slide thereon; and
a plurality of springs, one associated with each of said plunger rods and casings, and disposed to absorb the shock created by relative movement between said plunger rods and said plunger casings.

17. A stretcher as claimed in claim 16, wherein said plunger casings are rigidly joined together.

18. A stretcher as claimed in claim 17, wherein said plunger casings are joined together by a plate.

19. A stretcher as claimed in claim 16, wherein said backup cushion has a rigid plate as support, on which a hard foam molding is placed, said plate being attached to said plunger assembly.

20. A stretcher as claimed in claim 19, wherein said hard foam molding is covered with soft foam to cradle the patent's head and neck.

21. A stretcher as claimed in claim 20, wherein said hard foam molding and said soft foam are covered with leather.

22. A stretcher as claimed in claim 16, including:
a longitudinal belt attached to said backup cushion and extending generally the length of the stretcher;
an automatic take-up roller housing containing an automatic take-up roller, said housing being attached to said longitudinal belt;
a coupling belt operatively connected to said automatic take-up roller;
a coupling device attached to said coupling belt and which is adapted for engagement with compatible hook-like structure found on the floor of an ambulance, such that as said coupling device becomes engaged with the hook-like structure on the floor of an ambulance the tension exerted on the longitudinal belt by the movement of the stretcher away from said automatic take-up roller causes said automatic take-up roller to become locked, thereby locking said coupling belt at a fixed length.

23. A stretcher as claimed in claim 22, wherein said automatic take-up roller housing is fixed to a crosspiece disposed laterally on said stretcher, near the end of the stretcher adapted for receiving the patient's feet.

24. A stretcher as claimed in claim 22, wherein said longitudinal belt is divided into two sections near said backup cushion and is attached thereto on each side thereof.

25. A stretcher as claimed in claim 24, wherein said longitudinal belt may be detached from said backup cushion.

26. A stretcher as claimed in claim 25, wherein said backup cushion has a top and a bottom side and is adapted to be used on either side.

27. A stretcher as claimed in claim 26, wherein the top side of said cushion contains said hollow portion and the bottom side is smoothly cushioned.

28. A stretcher as claimed in claim 22, wherein said longitudinal belt is disposed underneath the portion of the stretcher used to directly support the patient.

29. A stretcher as claimed in claim 28, wherein said coupling device comprises a keeper loop which is adapted to automatically hook said compatible hook-like structure on the floor of an ambulance.

30. A stretcher as claimed in claim 28, wherein the length of the coupling belt rolled is limited such that in the rolled up condition said keeper loop is spaced just above the floor.

31. A stretcher as claimed in claim 28, wherein said longitudinal belt is attached to said automatic take-up roller housing such that it is in operative connection with a lock or a ratchet of said take-up roller.

32. A stretcher as claimed in claim 31, wherein said longitudinal belt is vertically hooked near said automatic take-up roller housing and attached thereto, such that one branch is operatively corrected to said lock and the other branch takes up the tension forces.

33. A stretcher as claimed in claim 32, wherein the branches of the fork of said longitudinal belt are attached to said automatic take-up roller housing such that as the angle of the branches with respect to said housing change, said lock of the automatic take-up roller becomes engaged.

34. A stretcher as claimed in either claim 11 or 16, wherein said backup cushion has a ridge adjacent said backup face means and extending upwardly therefrom to keep the patient's shoulders from riding up over said backup cushion.

* * * * *